United States Patent [19]

Sugawara et al.

[11] Patent Number: 4,642,601
[45] Date of Patent: Feb. 10, 1987

[54] HUMIDITY-SENSITIVE ELEMENT

[75] Inventors: Tooru Sugawara; Shigeki Tsuchitani; Noriyuki Kinjo; Shuichi Ohara, all of Hitachi, Japan

[73] Assignee: Hitachi, Ltd., Tokyo, Japan

[21] Appl. No.: 361,903

[22] PCT Filed: Jul. 20, 1981

[86] PCT No.: PCT/JP81/00166
§ 371 Date: Mar. 18, 1982
§ 102(e) Date: Mar. 18, 1982

[87] PCT Pub. No.: WO82/00362
PCT Pub. Date: Feb. 4, 1982

[30] Foreign Application Priority Data

Jul. 21, 1980 [JP] Japan .................................. 55-98815
Dec. 8, 1980 [JP] Japan ................................ 55-172054

[51] Int. Cl.⁴ .............................................. H01L 7/00
[52] U.S. Cl. ........................................ 338/35; 338/34; 73/336.5; 422/98; 422/94
[58] Field of Search .................... 338/35, 34; 73/336.5, 73/335, 23, 27 R; 422/98, 94

[56] References Cited

U.S. PATENT DOCUMENTS

| | | | |
|---|---|---|---|
| 2,728,831 | 12/1955 | Pope | 338/35 |
| 2,937,524 | 5/1960 | Gregor | 338/35 X |
| 3,073,161 | 1/1963 | Crabtree | 338/35 X |
| 3,167,734 | 1/1965 | Brucken et al. | 338/35 |
| 3,458,845 | 7/1969 | Thoma | 338/35 |
| 3,671,913 | 6/1972 | Mamiya et al. | 338/35 |
| 3,848,218 | 11/1974 | Wakabayashi et al. | 338/35 |
| 3,864,659 | 2/1975 | Furuuchi et al. | 422/98 |
| 3,891,958 | 6/1975 | Wakabayashi et al. | 338/35 |
| 4,263,576 | 4/1981 | Murata et al. | 338/35 |
| 4,386,336 | 5/1983 | Kinomoto et al. | 338/35 |

FOREIGN PATENT DOCUMENTS

| | | | |
|---|---|---|---|
| 50-020781 | 3/1975 | Japan | 338/35 |
| 53-034221 | 9/1978 | Japan | 338/35 |
| 54-080191 | 6/1979 | Japan | 338/35 |
| 54-26911 | 9/1979 | Japan | 338/35 |
| 381012 | 7/1973 | U.S.S.R. | 338/34 |

Primary Examiner—Clarence L. Albritton
Assistant Examiner—Marvin M. Lateef
Attorney, Agent, or Firm—Antonelli, Terry & Wands

[57] ABSTRACT

The humidity-sensitive element of this invention is composed of an insulating substrate (1), a pair of electrodes (2, 3) mounted thereon, and a humidity-sensitive material (8) covering the electrodes. The humidity-sensitive material (8) has a property to change its electric resistance depending on the moisture content in the atmosphere and is formed from fine particles each having a hydrophobic core and a hydrophilic group-containing surface layer covering the core. This humidity-sensitive element exhibits a nearly linear relationship between logarithm of electric resistance and relative humidity and small hysteresis, permitting a precise measurement of relative humidity. Insulating substrate (1) and electrodes (2,3) are preferred to form from an insulating layer of silicon semiconductor and conductive monosilicon formed on it, respectively. This permits size reduction of humidity-sensitive elements or devices.

33 Claims, 14 Drawing Figures

HUMIDITY-SENSITIVE ELEMENT

TECHNICAL FIELD

This invention relates to a humidity-sensitive element, a humidity-sensitive material, and a method of preparing them, and more particularly to a humidity-sensitive element utilizing a humidity-sensitive material of which electric resistance values change in response to a moisture content in surrounding gas (hereinafter, such a property of humidity-sensitive material is referred to as humidity-sensitive property), to the humidity sensitive materials, and to methods for preparing these material and element.

BACKGROUND ART

Methods of measuring relative humidity include mechanical and electrical methods. The latter is advantageous over the former in points of having the possibility of size reduction of instrument, rapid response, and easy conversion of humidity to electric signals. There is used an electric resistance type humidity-sensitive element utilizing the humidity-sensitive property of various materials in the electrical humidity measuring method. This humidity-sensitive element is constructed from an insulating substrate, a pair of electrodes arranged thereon, and a layer of humidity-sensitive material covering these electrodes.

The humidity-sensitive material conventionally used in such electric resistance type humidity-sensitive element is as follows:

(1) Ceramic materials.
(2) Electrolytes such as lithium chloride (LiCl).
(3) Hygroscopic resins containing dispersed conductive powder.
(4) Hydrophilic polymers or polyelectrolytes.
(5) Hydrophobic materials which is made hydrophilic by introducing cationic group into the molecule of hydrophobic polymers.

These types of humidity-sensitive materials had the following disadvantages, respectively:

Type (1): The moisture adsorption on these ceramic materials is partly due to chemisorption which is irreversible. Accordingly, the humidity-sensitive elements employing these humidity-sensitive materials exhibit significant hysteresis and poor response, and additionally tend to cause deformation on standing in a high humidity atmosphere for a long period of time.

Type (2): These materials cause deliquescence in a high humidity atmosphere and eventually flow out. Accordingly, the humidity-sensitive element employing these materials have extremely short life spans, and the range of humidity measurable for a single element of this type is narrow.

Type (3): These materials exhibit no humidity-sensitive property in a low humidity atmosphere. It is difficult to make the degree of dispersion of conductive powders uniform, and hence this type of humidity-sensitive element results in a low yield of production and is also poor in reliability.

Type (4): These materials are better than the above three types of material in humidity-sensitive property, but cause expansion or shrinkage depending upon the moisture content in the surrounding atmosphere because they absorb large amounts of moisture. For this reason, a layer of this type of materials used is liable to peel from the substrate or the electrode.

Type (5): These materials, disclosed in Japanese Patent Application Laid-open No. 80191/1979, have been developed in order to solve the problems involved in the above four types of materials. It is desirable to hold a linear relationship between the relative humidity values to be detected by this type of element and the logarithms of the corresponding electric resistances of the element, since the relative humidity is converted to electric signals on the basis of the relation between these two parameters. However, no linear relationship exists between them in humidity sensing element employing humidity-sensitive materials disclosed in said patent application, and additionally considerable hysteresis is exhibited thereby. This complicates the conversion circuit and produces large errors between measured and true humidity values.

It is further desired to reduce the electric resistance between electrodes, since a low value of the resistance reduces the disturbing effect of noises and as a result higher precision measurement can be expected.

DISCLOSURE OF THE INVENTION

An object of this invention is to provide a humidity-sensitive element which holds an almost linear relationship between relative humidity and logarithm of electric resistance and exhibits slight hysteresis, and a method of preparing the same.

Another object of the invention is to provide a highly reliable humidity-sensitive element which makes it easy to convert relative humidity values to electric signals, and a method of preparing the same.

A further object of the invention is to provide a humidity-sensitive element which can be made in a compact size in addition to having an almost linear relationship between relative humidity and logarithm of electric resistance and exhibiting slight hysteresis, and a method of preparing the same.

A still further object of the invention is to provide a humidity-sensitive material which has an almost linear relationship between relative humidity and logarithm of electric resistance, exhibits only slight hysteresis, and is adapted for humidity-sensitive elements, and a method of preparing the same.

The humidity-sensitive material of this invention is characterized by being an aggregate of fine particles which are each formed from a core having hydrophobicity (hereinafter, referred to simply as a hydrophobic core) and the core-enclosing surface layer of a compound having an ionic or hydrophilic group (hereinafter, the expressions "a compound having an ionic group" and "a compound having a hydrophilic group" are referred to as "an ionic compound" and "a hydrophilic compound", respectively).

The humidity-sensitive element of this invention is characterized by being a structure in which the film of the above-mentioned humidity-sensitive material covers a pair of electrodes mounted on an insulating substrate.

The insulating substrate is preferably made of a silicon semiconductor provided with an electric insulating layer.

The following methods have been confirmed as effective in preparing the humidity-sensitive material of this invention: The first method is characterized by synthesizing a polymer latex by emulsion copolymerization or a similar process in an aqueous solution (including plain water also; the same applies hereinafter) as the dispersion medium, followed by drying the latex to obtain a coagulated film which is a cluster of the polymer particles (said coagulated film is referred to as "latex film" hereinafter) wherein the surface layer of each particle is more ionic or more hydrophilic than the core portion of each particle (this method is referred to as "method A" hereinafter). The second method is characterized by synthesizing a hydrophobic polymer, followed by grafting an ionic, or hydrophilic organic compound on the polymer particle surface (this method is referred to as "method B" hereinafter).

The particles constructing the humidity-sensitive material of this invention, are each made of a core and a surface layer, as mentioned above. The shape of the core is not particularly restricted, that is, it is not limited to the sphere. It is allowed to be either the rod form or the plate form. However, the average particle size is preferably to be about 100 $\mu$m or less, since the space between the two electrodes of the humidity-sensitive element is desirable to be packed with the humidity-sensitive material film constructed with said particles and therefore the voids among said particles are desirably as small as possible.

The substance constituting the core suffices if it is hydrophobic and the substance constituting the surface layer suffices if it is ionic or hydrophilic. That is to say, either of these substances is not limited to polymers, and they may be formed from the same compound. When a polymer is used as the core or surface substance, it may be either linear or crosslinked one.

There is mentioned as an example of the particle structure a particle of the latex in which like a particle of the latex synthesized in an aqueous solution, hydrophobic portions are centered to constitute the core and ionic or hydrophilic portion are concentrated toward the surface to constitute the surface layer (this type of particle structure is referred to as A-type hereinafter). The particle substance may also be a copolymer of three or more kinds of monomer. In A-type of particle, the boundary between the core and surface layer is not always distinct, but it is certain that the surface layer is ionic or hydrophilic as compared with the core. In most particles ions are uniformly distributed in the surface layer. Particles of A-type may also contain small amounts of ionic or hydrophilic group in the core. Particles of the latex prepared in an aqueous solution by emulsion co-polymerization are advantageous in that the humidity-sensitive material of this invention can be obtained in a simple way because the particle surfaces naturally become hydrophilic.

Another example of the particle structure is that the core is a hydrophobic particle and a surface layer is formed thereupon by grafting an ionic or hydrophilic high molecular compound (this type of particle structure is referred to as B-type hereinafter). Particles of B-type are advantageous in that they maintain their shapes steadily on standing for many hours in an atmosphere of high temperature and high humidity, and the humidity sensitive property of the humidity-sensitive material is therefore kept stable.

Typical examples of substance constituting the particle core are polymers of nonionic vinyl compounds including ethylene, propylene, vinyl acetate, styrene, acrylic esters, methacrylic esters, vinyl halides, and monomers in use for rubbers, such as butadiene and chloroprene. Other examples of the core substance include copolymers of two or more kinds of vinyl monomers and further polycondensation products such as polyesters, polyamides, and polyurethanes; other poly- addition products; and mixtures of various kinds of hydrophobic compounds.

Compounds having at least one of ionic and hydrophilic characters suffice as a substance constituting the surface layer. However, for the purpose of obtaining a humidity-sensitive material of higher conductivity, ionic group containing compounds are preferred. They suffice whether the ionic group contained is anionic or cationic. In addition, it may be as well to use amphoteric latex particles of A-type. The ionic group may be either anionic or cationic one.

The anionic groups utilizable for said compounds include sulfonic acid group, carboxylic acid group phosphoric acid group, and their salt groups. More specifically, as examples of usable monomer containing such an anionic radical, there are cited styrene-sulfonic acid, acrylamidemthylpropanesulfonic acid, acrylic acid, methacrylic acid, and salts of these acids.

The cationic groups utilizable include groups of amines, salts thereof, quarternary ammonium salt, pyridinium salt, phosphonium salt, quarternary arsonium salt, quarternary stibonium salt, sulfonium salt, and iodinium salt. More particularly, as examples of usable monomer containing such a cationic group, there are mentioned 2-methacryloxyethyltrimethylammonium salt, vinylbenzyltrimethylammonium salt, trimethylvinylammonium salt, methacryloxyethyltri-n-butylammonium salt, vinylphenetyldimethylethylammonium salt, 4-vinyl-N-ethylpyridinium salt, 2-vinyl-N-methylpyridinium salt, vinyltriphenylphosphonium salt, vinyltripropylphosphonium salt, vinyltriphenylarsonium salt, vinyltrimethylstibonium salt, vinyldiethylsulfonium salt, vinylphenyliodinium salt. Ions usable as a counter ion for these cations include chloride, bromide, and iodide ions, and further fluoride, hydroxide, nitrate, acetate, and sulfate ions. Thus, the surface layer is constituted mainly with a polymer or copolymer of those prepared from these ionic monomers.

Furthermore, such a cationic group is also effective that can be prepared by copolymerizing a hydrophobic monomer with a tertiary amine monomer such as 2-dimethylaminoethylmetharylate to form latex particles, and quarternizing the nitrogen atoms of the latex particle surfaces with an alkylating agent such as methyl iodide.

On the other hand, hydrophilic compounds usable as a constituent of the particle surface layer include high-molecular compounds such as poly(vinyl alcohol) and poly(acrylamide).

Methods for preparing the humidity sensing material of this involve method A and method B as mentioned above. According to method A, a humidity-sensitive material which is an aggregate of particles of A-type is obtained and according to method B, a humidity-sensitive material which is an aggregate of particles of B-type is obtained.

An advantage of method A is that impurities having a significant adverse effect on the humidity sensitive property of humidity-sensitive material (e.g., ionic impurities affect the electric conductivity) can be removed with ease by dialysis or filtration using a filter of relatively large pore size.

An advantage of method B is that impurities can be removed in the same way as in method A either after hydrophobic latex particles as the cores have been synthesized or after the particle surface layers have formed.

In either method, A or B, the usual emulsion polymerization process or the emulsifier-less emulsion polymerization process is applied for synthesizing the latex particles.

When synthesizing the latex particles, it is possible to subject said particles to a cross-linking treatment, thereby the particle structure becoming stable over a long term. As a result, for instance, it is possible to prevent the humidity sensitive material from the rise of electric resistance, which would be caused by the mutual invasion of ionic groups and hydrophobic groups to the opponent domains.

Said cross-linking treatment is carried out in the following way: In the synthesis of latex particles by addition polymerization process, cross-linking is effected by copolymerization of a monomer having at least two polymerizable double bonds in the molecule, such as divinylbenzene or ethylene glycol dimethacrylate. Alternatively, after copolymerization of an epoxy group-containing monomer such as glycidyl methacrylate or allyl glycidyl ether with a hydrophobic monomer, crosslinking is effected with a dicarboxylic acid such as succinic acid or with a diamine such as ethylenediamine. In the synthesis of latex particles by condensation polymerization process, cross-linking is effected by using a multifunctional monner such as tricarballylic acid, glycerol, or tetraminodiphenylmethane. Other cross-linking treatments such as, $\gamma$-ray or electron beam irradiation and treatment with an oxidizing agent, such as potassium dichromate, followed by UV irradiation are effective.

In method B, the grafting of anionic or hydrophilic high-molecular weight compound onto the hydrophobic particles comprising a hydrophobic high-molecular weight compound is carried out in the following way: Initially, the hydrophobic particles are dispersed in such a polar solvent as to dissolve ionic or hydrophilic high-molecular compounds or such monomers, for example, in water or alcohol. Thereafter, active radicals are produced on the surfaces of said particles by oxidizing hydroxy group or isopropyl group present on the particle surfaces with cerium (IV) ammonium nitrate or oxygen. Then, grafting is effected utilizing said active groups as grafting sites by dissolving an ionic or hydrophilic monomer in said solvent. Besides this way, irradiation of $\gamma$-ray, electron beam, or U.V., light is effective as a means to produce grafting sites.

The humidity-sensitive materials of this invention obtained by the methods described above have, as shown in experimental results below, a humidity-sensitive property such that the relationship between electric resistance and relative humidity is nearly linear.

BRIEF DESCRIPTION OF THE DRAWINGS

Wherein FIGS. 5–7, 9, 10, and 14 are each a graph of humidity-sensitive property for illustrating the change of electric resistance of a humidity sensitive element with changing relative humidity;

FIG. 8 is a graph of humidity-sensitive property for illustrating the change of electric resistance with time of a humidity-sensitive element in an atmosphere of high temperature and high humidity; and FIGS. 11 and 12 are each a graph of response character of a humidity-sensitive element.

BEST MODE FOR CARRYING OUT THE INVENTION

Figure 1:
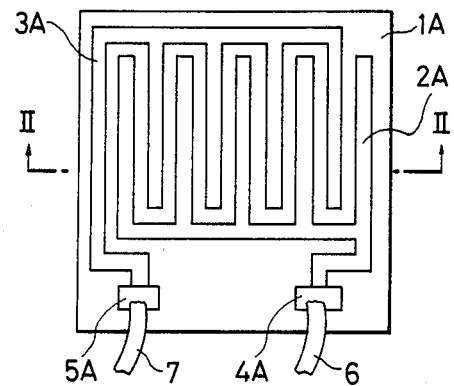
FIG. 1 is a diagrammatic plane view of a humidity-sensitive element for illustrating an embodiment of this invention.

Referring now to the drawings, embodiments of the humidity-sensitive element of this invention are illustrated.

Figure 2:
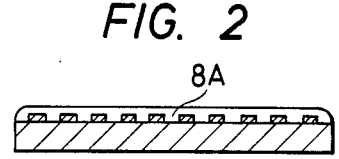
FIG. 2 is a sectional view taken on line II—II in FIG. 1.

In FIGS. 1 and 2, a pair of comb-shaped electrodes 2A and 3A is arranged on an insulating substrate 1A of square surface so as to be apart from each other by a definite distance. The electrodes 2A and 3A have respective ends formed into connecting terminals 4A and 5A, to which leads 6 and 7 are connected, respectively. The insulating substrate 1A and the electrodes 2A and 3A are covered with a coating 8A of humidity sensitive material, which has been formed in the same way as in a step 14 mentioned below. The insulating substrate 1A and the electrodes 2A and 3A are made of aluminum oxide and gold, respectively.

A humidity sensitive element best suited for size reduction is illustrated below as an embodiment of this invention.

Figure 3:
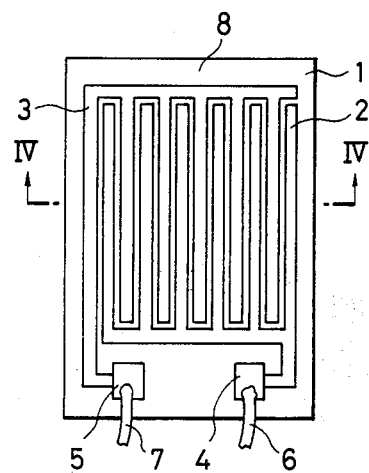
FIG. 3 is a diagrammatic plane view of a humidity-sensitive element for illustrating another embodiment of the invention.
Figure 4:
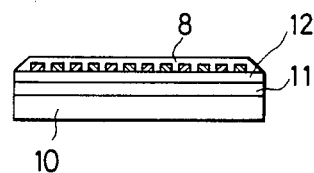
FIG. 4 is a sectional view taken on line IV—IV in FIG. 3.

In FIGS. 3 and 4, insulating substrate 1 comprises a silicon semiconductor substrate 10 and the first insulating layer 11 made of silicon dioxide ($SiO_2$) formed on the substrate 1. The first insulating layer 11 also has a shock absorbing function besides electric insulation. On the first insulating layer 11, the second insulating layer 12 made of silicon nitride ($Si_3N_4$) is formed. The insulating substrate 1 contains these two insulating layers. On the second insulating layer 12, a pair of electrodes 2 and 3 made of a phosphorus ion- or boron ion-injected polysilicon is arranged so as to have a short inter-electrode distance. Ends 4 and 5 of these electrodes 2 and 3 are formed from titanium, palladium, and gold into connecting terminals. On the second insulating layer 12 and the electrodes 2 and 3, a humidity sensitive material coating, i.e., humidity-sensitive layer 8 is formed.

Preparation process of said humidity-sensitive element is illustrated as follows:

Step 1: A silicon semiconductor wafer is washed to clear its surface.

Step 2: The first insulating layer of silicon dioxide of several hundred Å in thickness is formed on said wafer face by thermal oxidation.

Step 3: The second insulating layer of silicon nitride of several hundred Å in thickness is formed on the first insulating layer by the chemical vapor deposition method (hereinafter, referred to shortly as CVD method).

Step 4: A polysilicon layer of several microns in thickness is formed on the second insulating layer by CVD method.

Step 5: Boron ions or phosphorous ions are implanted into said polysilicon layer to reduce the electric resistance, thereby forming an electrode. Instead of ion implantation, diffusion method can be applied for ion injection.

Step 6: Unnecessary portions of said polysilicon layer are removed by photoetching to form a pair of comb-shaped polysilicon electrodes 2 and 3 having a short inter-electrode distance.

Step 7: Cutting portions of the silicon nitride is removed by photoetching.

In the above steps 6 and 7, other etching methods may also be applied instead of photoetching to fabricate the polysilicon and the silicon nitride.

Step 8: Titanium is vacuum evaporated on the ends of the electrodes.

Step 9: Palladium is vacuum evaporated on the deposited titanium.

Step 10: Gold is vacuum evaporated on the deposited palladium. Through these steps 8, 9, and 10, connecting terminals 4 and 5 having a top layer of gold are formed.

Step 11: Plural chips are cut off from the wafer.

Step 12: The chips are each set on a package.

Step 13: Leads are attached to the connecting terminals 4 and 5.

Step 14: Coating of a humidity-sensitive material is applied to form a humidity-sensitive layer 8.

Silicon nitride is suited for humidity-sensitive elements since it is a good electric insulator and at the same time has good water resistance. The silicon dioxide, though it becomes necessary when the humidity-sensitive element together with a measuring circuit is made up into one chip, may be removed when single sensors, i.e., single humidity-sensitive elements, are aimed.

Polysilicon is suited for electrodes of humidity-sensitive element since its resistivity can be reduced by implanting boron ions or phosphorous ions and in addition it withstands water and chemicals. The connecting terminals 4 and 5, which are each made of titanium, palladium, and gold layers, are unnecessary when a measuring circuit is formed on the same chip and the polysilicon electrodes are extended to the circuit.

Figure 14:
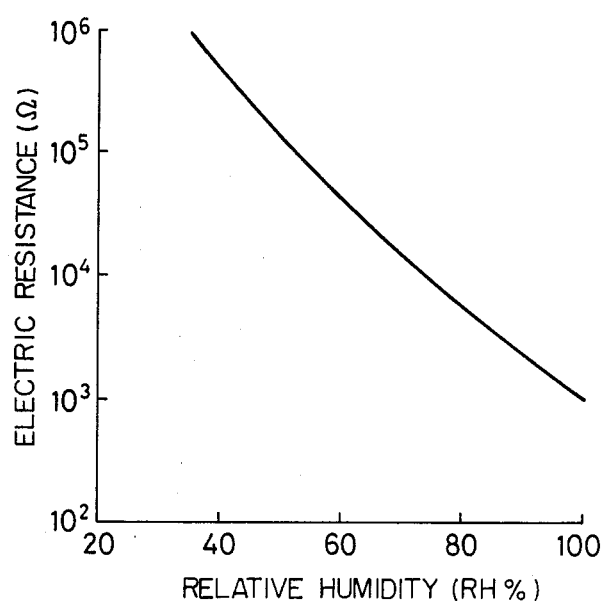

According to this preparation method, the interelectrode distance of a pair of polysilicon electrodes and the whole size of an element can be reduced to about 10 microns and 2 mm square or less, respectively. Comparing with conventional elements, this is smaller by about two orders in surface area. Nevertheless, electric resistance of the present elements is nearly equal to that of conventional elements. In order to compare the degree of this size reduction, there is shown in FIG. 14 an example of relative humidity-electric resistance relation measured on an element employing a sulfonated polystyrene resin as the humidity sensitive layer.

According to this embodiment, detection of the humidity in a narrow space is possible; a humidity sensor having long-term stability can be obtained because the sensor has electrodes of polysilicon and insulating layer of silicon nitride, both materials being water resistant, and the connecting terminals of the electrodes are constructed with titanium, palladium, and gold, which are anticorrosive; and the humidity sensor is not subjected to the influence of the noises due to extrinsic factors, because it can be assembled together with a measuring circuit into one chip (for this purpose, a silicon substrate is employed).

Coating of a humidity-sensitive material in step 14 is effected using a liquid dispersion of the material. Said liquid dispersion is a latex containing dispersed particles of A-type or B-type. For example, a latex synthesized by method A is used. The way to coat is suitably selected from spraying, brushing, immersion, spinner coating, etc. depending upon viscosity of latex, surface area of substrate, amount of production, etc. After coating, drying is effected by airing with air or nitrogen, thereby the latex particles adhere one another to form a continuous film. According to this drying way, the latex particles themselves and the film made of the particles do not break.

The present humidity-sensitive elements have such an effect as reliability and simplicity in conversion of detected humidity to an electric signal.

The electric resistance values of the present humidity-sensitive materials are low, and the humidity-sensitive elements employing these therefore rarely pick up noises. For instance, if a substance, such as dust, having an effect on the conductivity of humidity-sensitive material adheres, high-precision detection of humidity is still possible.

The present humidity-sensitive material film does not cause expansion or shrinkage because of the low moisture absorption of the cores of particles constituting the film, and as a consequence, the film rarely peels off from the substrate. Accordingly, long life span can be expected for the present humidity-sensitive elements.

The humidity sensitive materials of this invention will be illustrated in more detail by the following examples and comparative examples.

EXAMPLE 1

(method A)

To 500 ml water were added 0.1 ml of methyl methacrylate as a hydrophobic monomer, 0.01 mol of sodium stylenesulfonate as an anionic monomer and emulsifier, and 0.001 mol of potassium persulfate as a polymerization initiator. The liquid temperature was raised to 60° C. and emulsion copolymerization was carried out in nitrogen atmosphere under high speed stirring. Thus, a latex containing dispersed particles of A-type was obtained. Each particle had a core of poly(methyl. methacrylate) and a surface layer of sodium salt of poly(styrenesulfonic acid).

Said latex was purified by dialysis for two months using a dialysis tube of cellophane.

The purified latex was coated on a substrate, shown in FIGS. 1 and 2, of 20 mm×20 mm size (hereinafter, referred to as substrate I) and dried by airing to obtain a humidity-sensitive element No. 1. The weight of the coating 8A was about 3 mg.

Figure 5:
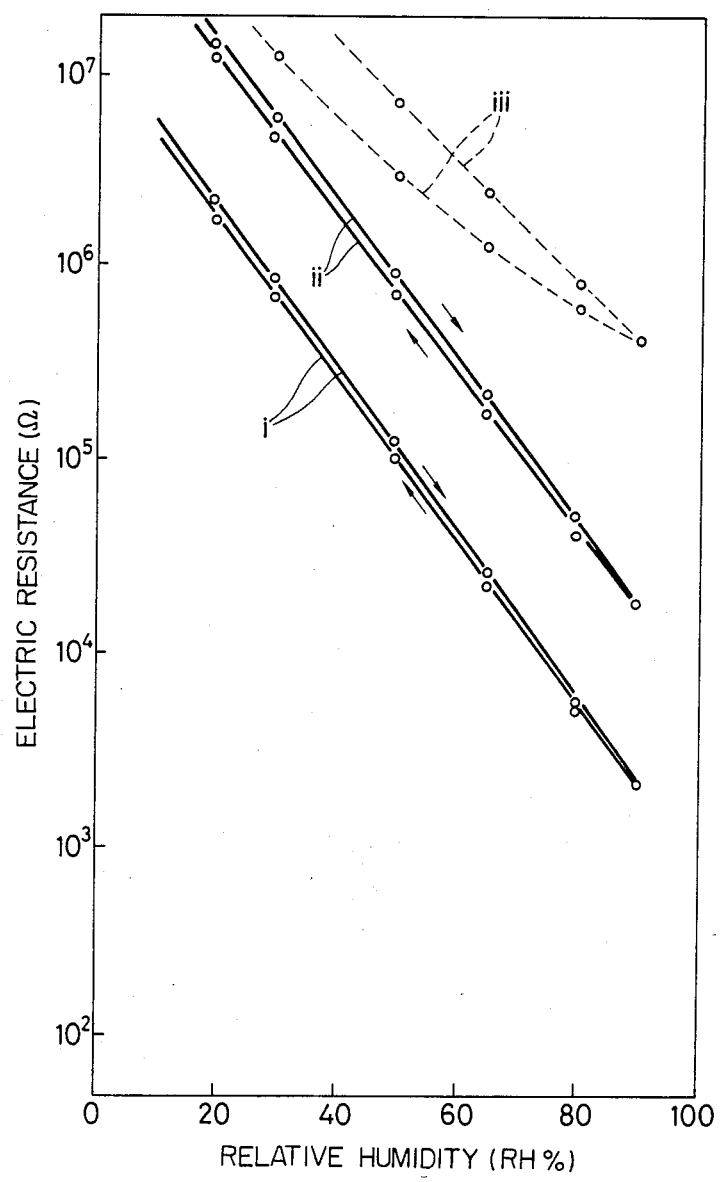
FIGS. 5–13 are each a graph of humidity-sensitive property of the humidity-sensitive element in an example for carrying out the invention.

Referring to humidity-sensitive property of the element No. 1, a nearly linear relation is held between relative humidity and electric resistance in both the absorption course and desorption course as shown by solid-line 1 in FIG. 5, and the hysteresis also is small.

EXAMPLE 2

(Method A)

The latex synthesized in Example 1 was treated with a cation exchange resin to obtain its acid-form.

It was purified by dialysis in the same manner as in Example 1, then coated on substrate I, and a humidity-sensitive element No. 2 was obtained through drying by airing.

The weight of the coating was about 3 mg.

Referring to the humidity-sensitive property of the element No. 2, a nearly linear relationship is held between relative humidity and electric resistance in both the absorption course and desorption course, as shown by solid line II in FIG. 5, and the hysteresis also is small.

COMPARATIVE EXAMPLE 1

After water was evaporated from the latex prepared in Example 2, the residue was dissolved in dimethylacetamide with the result that the structure of latex particles collapsed and the polymer dissolved in the solvent homogeneously.

This homogeneous solution was coated on substrate I so that the weight of coating 8A might be about 3 mg, and then a humidity-sensitive element No. 3 was obtained by 5 hours drying at 100° C.

Referring to the humidity-sensitive property of the element No. 3, the relationship between relative humidity and electric resistance is not linear either in the absorption course or in the desorption course as shown by broken line iii in FIG. 5, and in addition the hysteresis and electric resistance are obviously large as compared to the elements No. 1 and No. 2.

EXAMPLE 3

(Method A)

To 500 ml water were added 0.1 mol of styrene as a hydrophobic monomer, 0.05 mol of styrenesulfonic acid as an anionic monomer and emulsifying agent, and 0.01 mol of potassium persulfate as a polymerization initiator. The liquid temperature was raised to 60° C. and emulsion copolymerization was carried out in nitrogen atmosphere under high speed stirring. Thus, a latex containing dispersed particles of A-type was obtained. Each particle had a core of polystyrene and a surface layer of poly(styrenesulfonic acid).

Said latex was purified by dialysis for two months using a dialysis tube of cellophane.

The purified latex was coated on a substrate, shown in FIGS. 3 and 4, of 5 mm×5 mm size (hereinafter, referred to as substrate II) and dried by airing to obtain a humidity-sensitive element No. 4. The weight of the coating 8 was about 0.2 mg.

Figure 6:
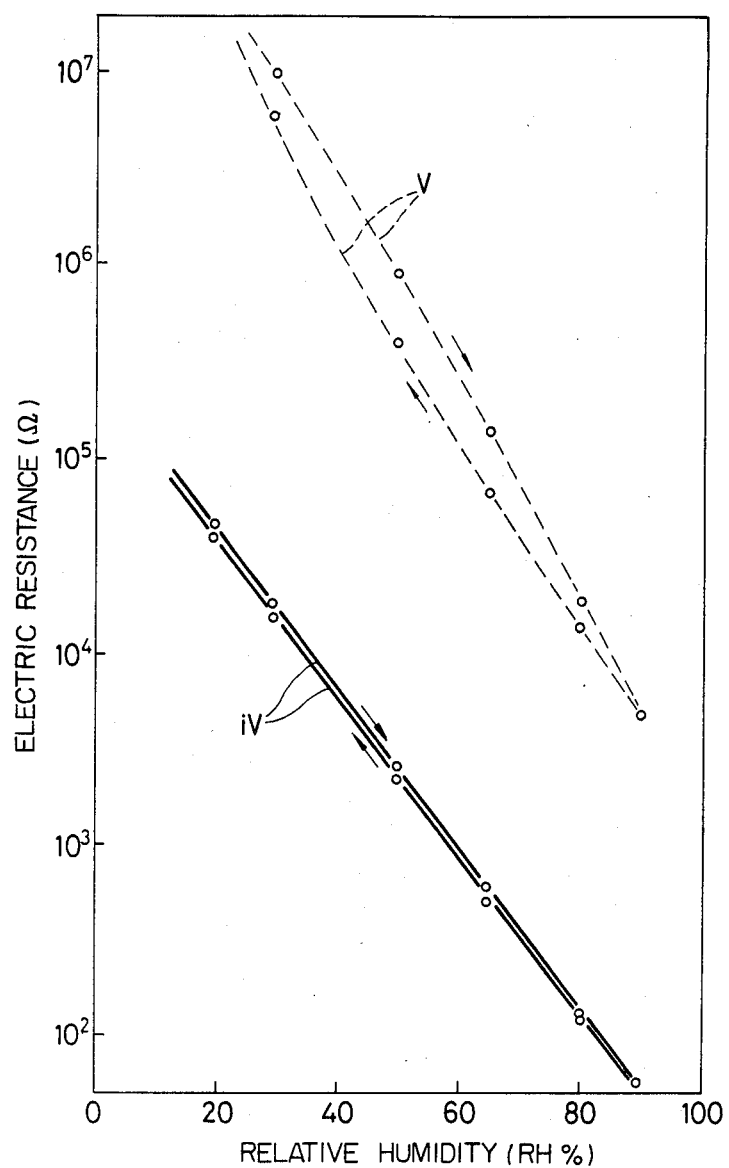

The humidity-sensitive property of the element No. 4 is almost linear in the relation between relative humidity and electric resistance in both the absorption course and desorption course as shown by solid line IV in FIG. 6, and the hysteresis also is small.

COMPARATIVE EXAMPLE 2

The humidity-sensitive element No. 4 prepared in Example 3 was left for 1 month under the saturated mixed vapor pressure of dimethylacetamide and water at 90° C., whereby the structure of the latex particle was almost broken and a humidity-sensitive element No. 5 was obtained.

Referring to the humidity-sensitive property of the element No. 5, no good linearity is seen in the relation between relative humidity and electric resistance either in the absorption process or in the desorption process as shown by broken line V in FIG. 6. In addition, the hysteresis and electric resistance are obviously large.

As can be seen from the comparison of the humidity-sensitive elements No. 1 and No. 2 with No. 3 and of No. 4 with No. 5, the humidity-sensitive material of this invention has low electric resistance as compared with the humidity-sensitive material formed from a uniform polymer which has the same chemical composition as the sensitive material of this invention. This high electric resistance in the case of uniform polymer is attributable to the possible inhibition of the moisture absorption and dissociation of ionic groups by the effect of hydrophobic groups. In the sensitive material formed from a uniform polymer, if the concentration of ionic group is enhanced in order to reduce the electric resistance, the sensitive material coating would peel from the substrate by the swelling and shrinkage due to moisture absorption and desorption.

EXAMPLE 4

(Method A)

To a solvent composed of 250 ml ethanol and 250 ml water, there were added 0.1 mol of $\beta$-hydroxyethyl methacrylate as a hydrophobic monomer, 0.04 mol of sodium acrylate as an anionic monomer and emulsifier, and 0.001 mol of sodium hydrogensulfite as a polymerization initiator. The liquid temperature was raised to 60° C. and emulsion copolymerization was carried out in nitrogen atmosphere under high speed stirring. Thus, a latex containing dispersed particles of A-type was obtained. Each particle had a core of poly($\beta$-hydroxyethyl methacrylate) and a surface layer of poly(sodium acrylate).

The latex was purified by dialysis in the same manner as in Example 1, then coated on substrate I, and dried by airing to obtain a humidity-sensitive element No. 6 having about 3 mg of coating 8A.

Figure 7:
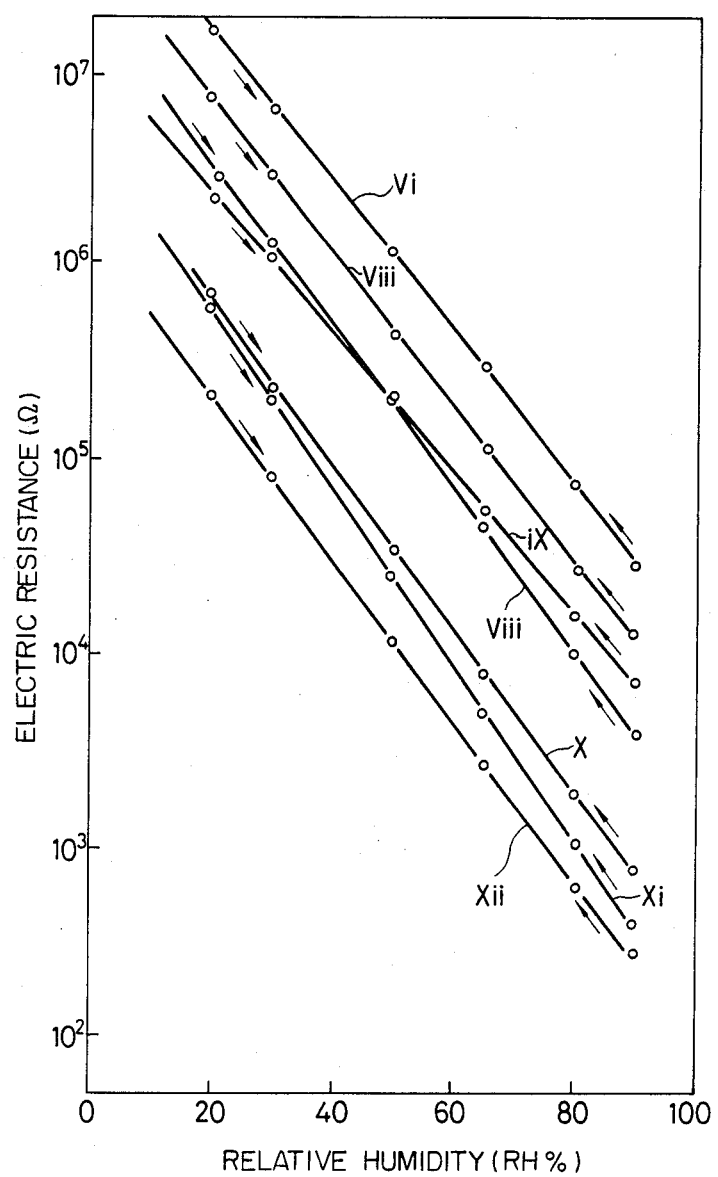

The humidity-sensitive property of the element is shown by solid line VI in FIG. 7.

EXAMPLES 5

(METHOD A)

To 500 ml water were added 0.1 mol of methyl acrylate as hydrophobic monomer, 0.02 mol of potassium methacrylate as an anionic monomer and emulsifier, and 0.001 mol of sodium hydrogensulfite as a polymerization initiator. Emulsion copolymerization was carried out in the same manner as Example 4 and the latex obtained was purified by dialysis in the same manner as Example 4.

This latex was coated on substrate I and a humidity-sensitive element No. 7 was obtained in the same manner as Example 4. Its humidity-sensitive property is shown by solid line vii in FIG. 7.

EXAMPLE 6

(METHOD A)

To 500 ml water were added 0.06 mol of styrene and 0.04 mol of butadiene as hydrophobic monomers, 0.005 mol of sodium 9-acrylamidestearate as a hydrophilic monomer and emulsifier, and 0.0001 mol of sodium persulfate and 0.00008 mol of sodium carbonate as polymerization initiators. Emulsion copolymerization was carried out in the same manner as Example 4 and the latex obtained was purified by dialysis in the same manner as Example 4.

This latex was coated on substrate II in the same manner as Example 4, and a humidity-sensitive element No. 8 was obtained. Its humidity-sensitive property is shown solid line viii in FIG. 7.

EXAMPLE 7

(METHOD A)

To 500 ml water were added 0.1 mol of ethyl methacrylate as a hydrophobic monomer, 0.03 mol of lithium 2-acrylamide-2-methylpropanesulfonate as a hydrophilic monomer and emulsifier, and 0.001 mol of sodium hydrogensulfite as a polymerization initiator. Emulsion copolymerization was carried out in the same manner as Example 4, and the latex obtained purified by dialysis in the same manner as Example 4.

This latex was coated on substrate II in the same manner as Example 4 and a humidity-sensitive element No. 9 was obtained. Its humidity-sensitive property is shown by solid line ix in FIG. 7.

EXAMPLE 8

(METHOD A)

To 500 ml water were added 0.1 mol of styrene and 0.01 mol of N,N'-diethylaminoethyl methacrylate as hydrophobic monomers, 0.01 mol of methacrylic acid as an anionic monomer and emulsifier, and 0.015 mol of potassium persulfate as a polymerization initiator. Emulsion copolymerization was carried out in the same manner as Example 4, and the latex obtained was purified by dialysis in the same manner as Example 4.

This latex was coated on substrate II, and in the same as Example 4, a humidity-sensitive element No. 10 was obtained. Its humidity-sensitive property is shown by solid line x in FIG. 7.

EXAMPLE 9

(METHOD A)

To 500 ml water were added 0.1 mol of styrene as a hydrophobic monomer, 0.005 mol of N-methylvinylpyridinium bromide as a cationic monomer and emulsifier, and 0.001 mol of azobisisobutylamidine hydrochloride as a polymerization initiator. Emulsion copolymerization was carried out in the same manner as Example 4 and the latex obtained was purified by dialysis in the same manner as Example 4.

This latex was coated on substrate II and in the same manner as Example 4, a humidity-sensitive element No. 11 was obtained. Its humidity-sensitive property is shown by solid line xi in FIG. 7.

EXAMPLE 10

(METHOD A)

To 500 ml water were added 0.2 mol of methyl methacrylate as a hydrophobic monomer, 0.05 mol of methacryloxyethyltrimethylammonium chloride as a cationic monomer and emulsifier, and 0.002 mol of azobisisobutylamidine as a polymerization initiator. Emulsion copolymerization was carried out in the same manner as Example 4 and the latex obtained was purified by dialysis in the same manner as Example 4.

This latex was coated on substrate II and in the same manner as Example 4, a humidity-sensitive element No. 12 was obtained. Its humidity sensitive property is shown by solid line xii in FIG. 7.

EXAMPLE 11

(METHOD A)

To 500 ml water were added 0.2 mol of methyl methacrylate as a hydrophobic monomer, 0.1 mol of sodium acrylamide-2-methylpropanesulfonate as an anionic monomer, and 0.001 mol of potassium persulfate as a polymerization initiator. The liquid temperature was brought to 70° C. and emulsion copolymerization was carried out for 8 hours in nitrogen atmosphere under high-speed stirring. Thus, a latex of A-type was obtained. Each particle of the latex had a core of poly(methyl methacrylate) and a surface layer of sodium acrylamide-2-methylpropanesulfonate polymer.

This latex was purified by dialysis in the same manner as Example 1, coated on substrate I, and a humidity-sensitive element No. 13 having about 5 mg of coating 8A was obtained after drying by airing.

Figure 8:
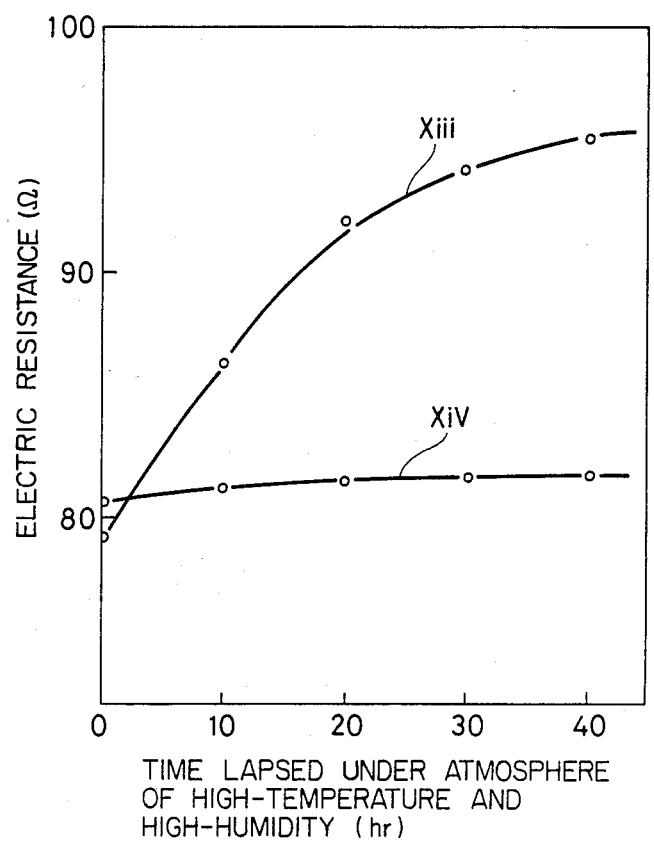

The change of electric resistance with time of this humidity-sensitive element No. 13 where it was left under high temperature-high humidity conditions of 50° C. and of 90% relative humidity is shown by solid line xiii in FIG. 8.

EXAMPLE 12

(METHOD B)

To 500 ml water were added 0.2 mol of methyl methacrylate as a hydrophobic monomer, 0.01 mol of ethylene glycol dimethacrylate as a cross-linking agent, 0.02 mol of hydroxyethyl methacrylate as a grafting site-giving monomer, and 0.01 mol of sulfurous acid as a polymerization initiator. With the liquid temperature brought to 60° C., copolymerization was carried out in the air for 10 hours while stirring at a high speed. The resultant latex contained dispersed particles of a methyl methacrylate-hydroxyethyl methacrylate copolymer cross-linked with ethylene glycol dimethacrylate. To this latex were further added 0.01 mol of cerium (IV) ammonium nitrate as a graft polymerization initiator and 0.1 mol of sodium acrylamide-2-methylpropanesulfonate as an anionic, grafting monomer. The liquid temperature was brought to 50° C. and graft polymerization was carried out for 6 hours in nitrogen atmosphere while stirring at a high speed. Thus, a latex of B-type was obtained.

This latex was purified by dialysis in the same manner as Example 1, then coated on substrate I, and the coating was dried by airing. Thus, a humidity-sensitive element No. 14 having about 5 mg of coating 8A was obtained.

The change of electric resistance with time of this humidity-sensitive element No. 14, when it was left under an atmospheric condition of 50° C. and 90% relative humidity, is shown by solid line xiv in FIG. 8.

This sensitive element No. 14 is more stable than the element No. 13 prepared by method A, that is, the electric resistance of the element No. 14 is almost constant on standing for many hours under high temperature-high humidity condition.

EXAMPLE 13

(METHOD B)

To 500 ml water were added 0.2 mol of acrylonitrile as a hydrophobic monomer, 0.02 mol of allyl glycidyl ether and 0.02 mol of aminoethyl methacrylate as cross-linking agents, 0.01 mol of hydroxyethyl methacrylate as a graft cite-giving monomer, and 0.001 mol of azobisisobutylamidine hydrochloride as a polymerization initiator. With the liquid temperature brought to 70° C., copolymerization and cross-linking were carried out at the same time for 10 hours in nitrogen atmosphere while stirring at a high speed.

Then, to the resultant latex were added 0.01 mol of cerium (IV) ammonium nitrate as a graft polymerization initiator and 0.1 mol of methacryloxyethyltrimethylammonium bromide as a cationic, grafting monomer.

With the liquid temperature brought to 50° C., graft polymerization was carried out for 6 hours in nitrogen atmosphere while stirring at a high speed. Thus, a latex containing dispersed particle of B-type was obtained. The surface layer of each particle was made up of the cationic polymer.

This latex was purified by dialysis in the same manner as Example 1, coated on substrate I, and dried by airing. Thus, a humidity-sensitive element, No. 15, having about 5 mg of coating 8A was obtained.

Figure 9:
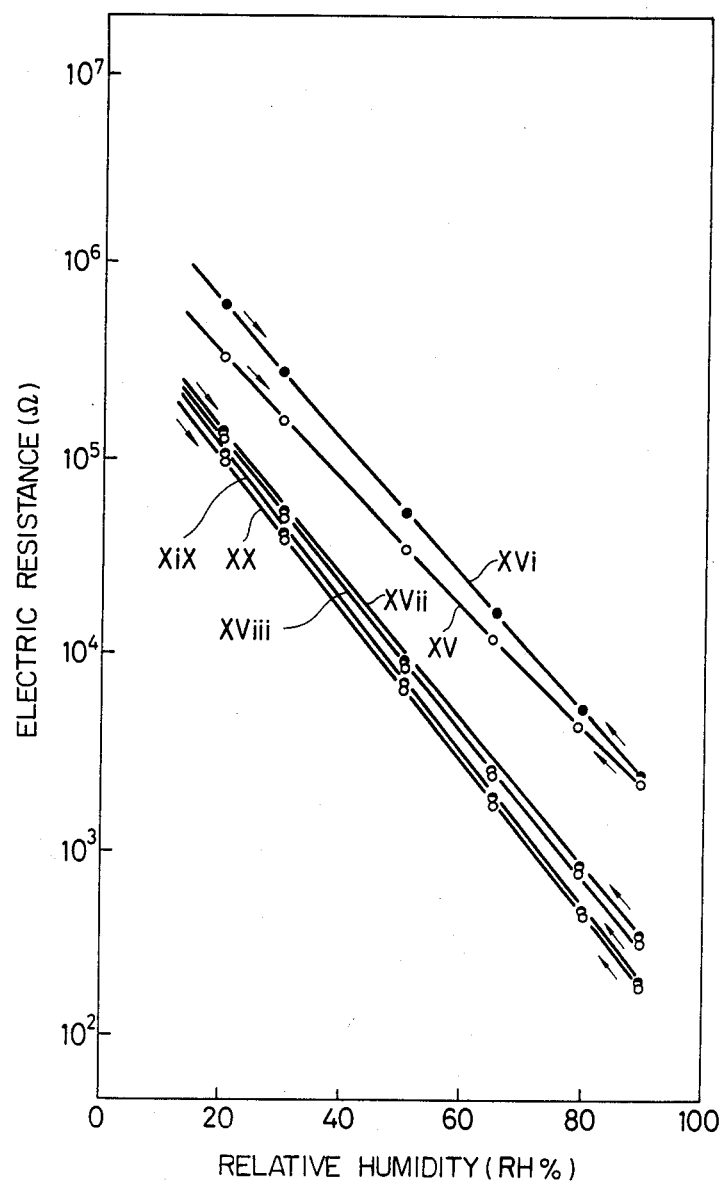

The humidity-sensitive property of the element No. 15 measured after it had been left in the atmospheric conditions of 50° C. and 90% relative humidity for 20 hours is shown by solid line XV in FIG. 9, wherein solid line xvi represents that of the same element but unexposed to any such condition.

EXAMPLE 14

(METHOD B)

To 500 ml water were added 0.2 mol of methyl acrylate as a hydrophobic monomer, 0.02 mol of glycidyl methacrylate and 0.02 mol of methacrylic acid as cross-linking agents, 0.01 mol of hydroxyethyl methacrylate as a graft site-giving monomer, and 0.01 mol of sodium hydrogensulfite and 0.001 mol of ferric hydroxide as polymerization initiators. With the liquid temperature brought to 50° C., copolymerization was carried out for 8 hours in nitrogen atmosphere while stirring at a high speed. The resultant latex was subjected to cross-linking reaction at 80° for 10 hours by adding 0.001 mol of triethylamine as a cross-linking catalyst. Then, 0.01 mol of cerium (IV) ammonium nitrate as a graft polymerization initiator and 0.1 mol of sodium methacrylate as a grafting anionic monomer were added thereto. With the liquid temperature brought to 50° C., graft polymerization was carried out for 6 hours in nitrogen atmosphere while stirring at a high speed. Thus, a latex containing dispersed particles of B-type was obtained.

This latex was purified by dialysis in the same manner as Example 1, coated on substrate 1, and dried by airing.

Thus, a humidity-sensitive element No. 16 having about 5 mg of coating 8A was obtained.

The humidity sensitive property of the element No. 16 which had been left for 20 hours in an atmosphere of 50° C. and of 90% relative humidity is shown by solid line xvii in FIG. 9, wherein solid line xviii represents that of the same element but measured before said exposure test.

As can been seen from FIG. 9, the sensitive element No. 16 is very stable even when left under the conditions of high temperature and high humidity, as compared with the element No. 15.

EXAMPLE 15

(METHOD B)

To 500 ml water were added 0.1 mol of styrene as a hydrophobic monomer, 0.01 mol of divinylbenzene as a cross-linking agent, 0.1 mol of p-isopropylstyrene as a graft site-giving monomer, and 0.002 mol of sodium hydrogensulfite and 0.001 mol of potassium persulfate as polymerization initiators. With the liquid temperature brought to 50° C., copolymerization was carried out for 10 hours in nitrogen atmosphere while stirring at a high speed. The resultant latex contained dispersed particles of a styrene-p-isopropylstyrene copolymer cross-linked with divinylbenzene. The latex was heated to 80° C. and oxygen was blown thereinto for 10 hours to peroxidize isopropyl groups of the latex particle surface. Then, 0.1 mol of sodium styrenesulfonate as a grafting anionic monomer and 0.01 mol of dimethylaniline as a promotor were added to the latex, and graft polymerization was carried out at 60° C. for 10 hours in nitrogen atmosphere while stirring at a high speed.

Thus, a latex containing dispersed particles of B-type was obtained.

The latex was purified by dialysis in the same manner as Example 1, coated on substrate I, and dried by airing. Thus, a humidity-sensitive element No. 17 having about 5 mg of coating 8A were obtained.

The humidity-sensitive property of the element No. 17 measured after it had been left in the atmospheric conditions of 50° C. and 90% relative humidity for 20 hours is shown by solid line xix in FIG. 9, wherein solid line xx represents that of the same element but measured before said exposure test.

As can be seen from FIG. 9, also the sensitive element No. 17 is very stable even when left under such high temperature and high humidity conditions.

EXAMPLE 16

(METHOD A)

To 300 ml water were added 0.2 mol of methyl methacrylate as a hydrophobic monomer, 0.1 mol of 2-methacryloxyethyltrimethylammonium iodide as a cationic monomer and emulsifier, and 0.001 mol of azobisisobutylamidine hydrochloride as a polymerization initiator. With the liquid temperature brought to 60° C., emulsion polymerization was carried out for 10 hours in nitrogen atmosphere while stirring at a high speed. Thus, a latex containing dispersed particles of A-type was obtained. Each particle had a core of poly(-methyl methacrylate) and a surface layer of 2-methacryloxyethyltrimethylammonium iodide polymer, which contains crimethylammonium group as a cationic group.

This latex was purified by dialysis in the same manner as Example 1, then coated on substrate I, and dried by airing. Thus, a humidity sensing element, No. 18, was obtained, of which the coating 8A weighed about 5 mg.

Figure 10:
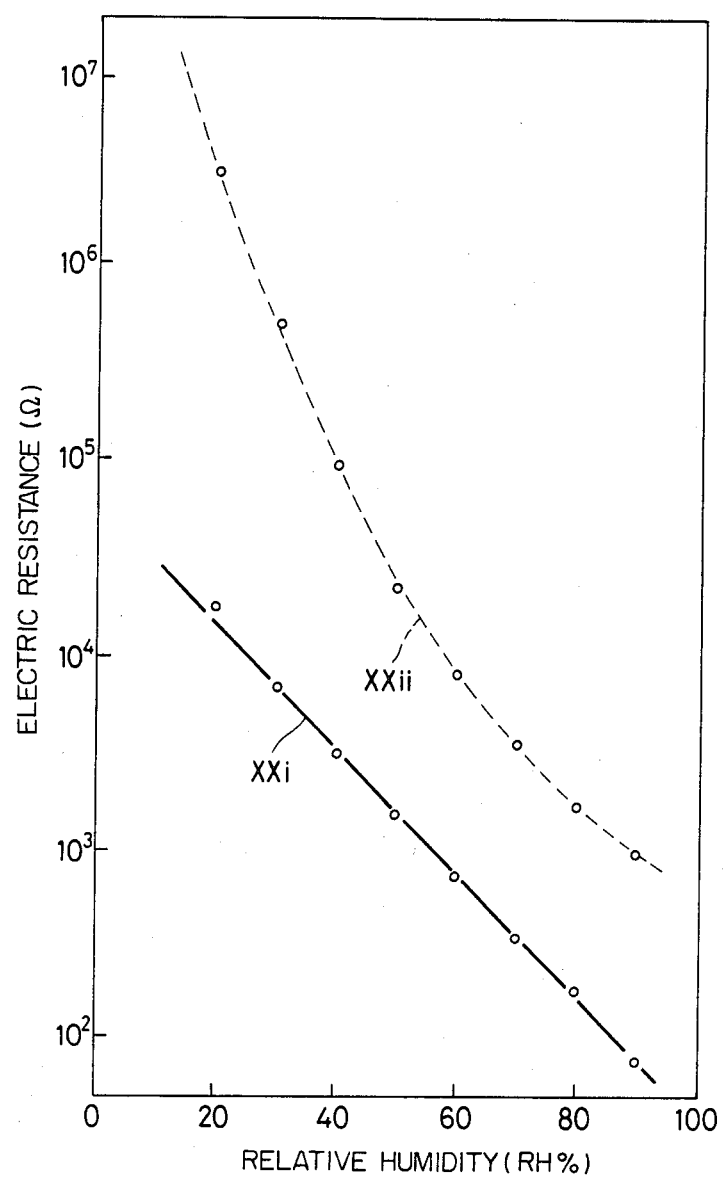

The humidity-sensitive property of the element No. 18 is shown in FIG. 10 by solid line xxi.

COMPARATIVE EXAMPLE 3

Solution copolymerization was carried out using the same reagents in the same amounts under the same conditions as Example 16, except that 300 ml of methanol was used in place of 300 ml of water. As a result, a homogeneous solution of cationic polyelectrolyte was obtained.

This homogeneous solution was coated on substrate I so as to give a weight of 5 mg of coating 8A, and after drying by airing, a humidity-sensitive element No. 19 was obtained.

The humidity-sensitive property of the element No. 19 is such that the relation between relative humidity and electric resistance is far from linear in both courses, moisture absorption and desorption, as shown in FIG. 10 by broken line xxii.

In addition, this element shows electric resistance values higher by about one decimal than those of the element No. 18.

EXAMPLE 17

(METHOD A)

To 300 ml water were added 0.2 mol of styrene as a hydrophobic monomer, 0.1 mol of sodium styrenesulfonate as an anionic monomer and emulsifier, and 0.001 mol of potassium persulfate as a polymerization initiator.

Then, emulsion polymerization was carried out at 60° C. for 10 hours in nitrogen atmosphere while stirring at a high speed. As a result, a latex containing dispersed polymer particles of A-type was obtained. Each particle had a core of polystyrene and a surface layer containing sulfonate groups which are anionic.

This latex was purified by dialysis in the same manner as Example 1, then coated on substrate I, and dried by airing. Thus, a humidity-sensitive element, No. 20, was obtained, of which the coating 8A weighed about 5 mg.

Figure 11:
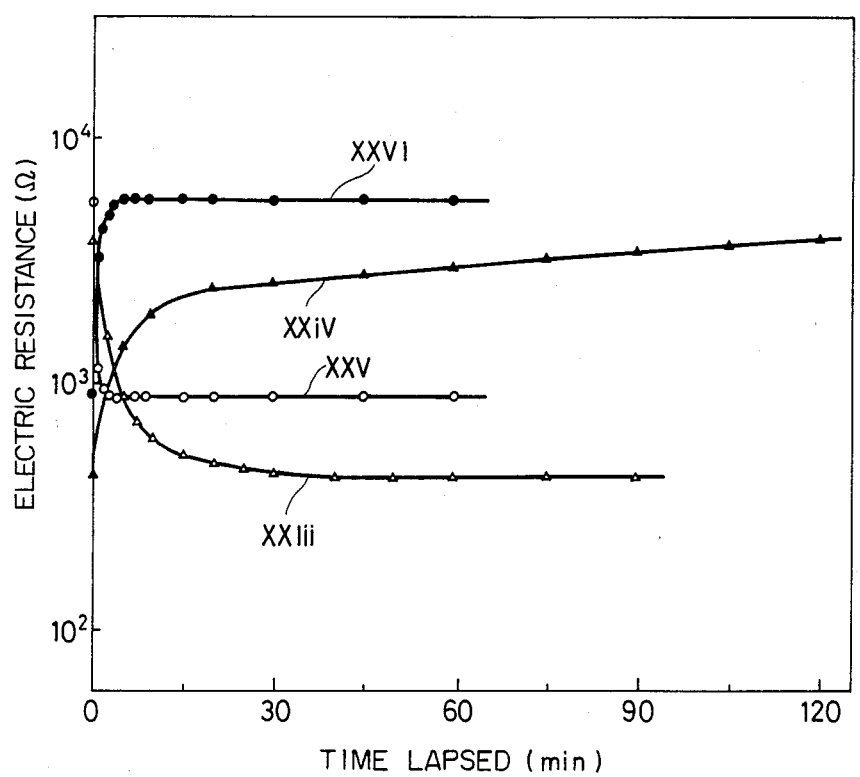

The response characteristic of the element No. 20 is shown in FIG. 11, wherein solid line xxiii indicates the response in the process of moisture absorption where relative humidity is increased from 40 to 60%, and solid line xxiv indicates the response in the process of moisture desorption where relative humidity is decreased from 60 to 40%.

EXAMPLE 18

(METHOD A)

To 300 ml water were added 0.2 mol of styrene as a hydrophobic monomer, 0.1 mol of vinylbenzyltrimethylammonium chloride as a cationic monomer and emulsifier, and 0.001 mol of azobisisobutylamidine hydrochloride, and emulsion copolymerization was carried out in the same manner as Example 17. Dispersed particles of A-type in the resultant latex have each a core of polystyrene and a surface layer containing trimethylammonium groups, which are cationic.

This latex was purified by dialysis in the same manner as Example 1, then coated on substrate I, and dried by airing. Thus, a humidity-sensitive element No. 21 was obtained, of which the coating 8A weighed about 5 mg.

Figure 12:
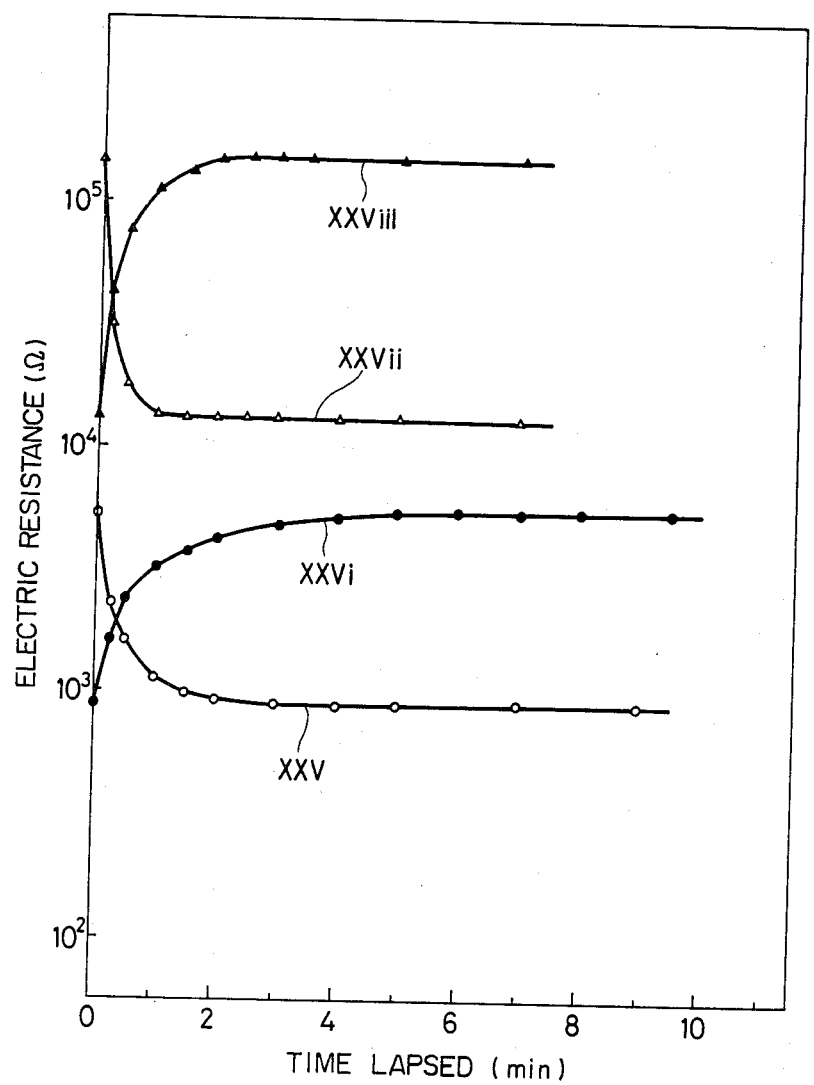

The response characteristic of the element No. 21 is shown in FIGS. 11 and 12, wherein solid line xxv indicates the response in the course of moisture absorption where relative humidity is increased from 40 to 60%, and solid line xxvi indicates the response in the course of moisture desorption where relative humidity is decreased from 60 to 40%.

As can be seen from these curves, the element No. 21 exhibits very rapid response, the time required for electric resistance value to reach equilibrium being only about 3 minutes in the course of moisture absorption and about 5 minutes in the course of moisture desorption. In addition, the equilibrium value of electric resistance shown after moisture desorption has been completed agrees with the initial value thereof shown before moisture absorption. From this the element No. 21 proves to have no hysteresis.

EXAMPLE 19

(METHOD A)

A humidity-sensitive element No. 22 was obtained by coating the latex prepared and purified by dialysis in Example 2, on substrate I so as to give a weight of about 1 mg of the coating 8A.

The response characteristic of the element No. 22 is shown in FIG. 12, wherein solid line xxvii indicates the response in the course of moisture absorption where relative humidity is increased from 40 to 60%, and solid line xxviii indicates the response in the course of moisture desorption where relative humidity is decreased from 60 to 40%.

As is obvious from comparing with the values of the element No. 21, a low coating weight results in an electric resistance. On the other hand, this results in shorter response time, that is, the response time of the element No. 22 is about 1.5 minutes in moisture absorption course and about 2.5 minutes in moisture desorption course.

EXAMPLE 20

(METHOD A)

To 300 ml water were added 0.2 mol of 4-vinylpyridine as a hydrophobic monomer, 0.1 mol of 4-vinyl-N-ethylpyridinium bromide as a cationic monomer, 0.02 mol of divinylbenzene as a cross-linking agent, and 0.001 mol of azobisisobutylamidine hydrochloride as a polymerization initiator, and emulsion polymerization was carried out in the same manner as Example 17. The resultant latex particles each had a core of cross-linked poly(4-vinylpyridine) and a surface layer containing pyridinum proups, which are cationic.

This latex was purified by dialysis in the same way as Example 1, then coated on substrate I, and dried by airing. Thus, a humidity-sensitive element No. 23 was obtained, of which the coating 8A weighed about 5 mg.

Figure 13:
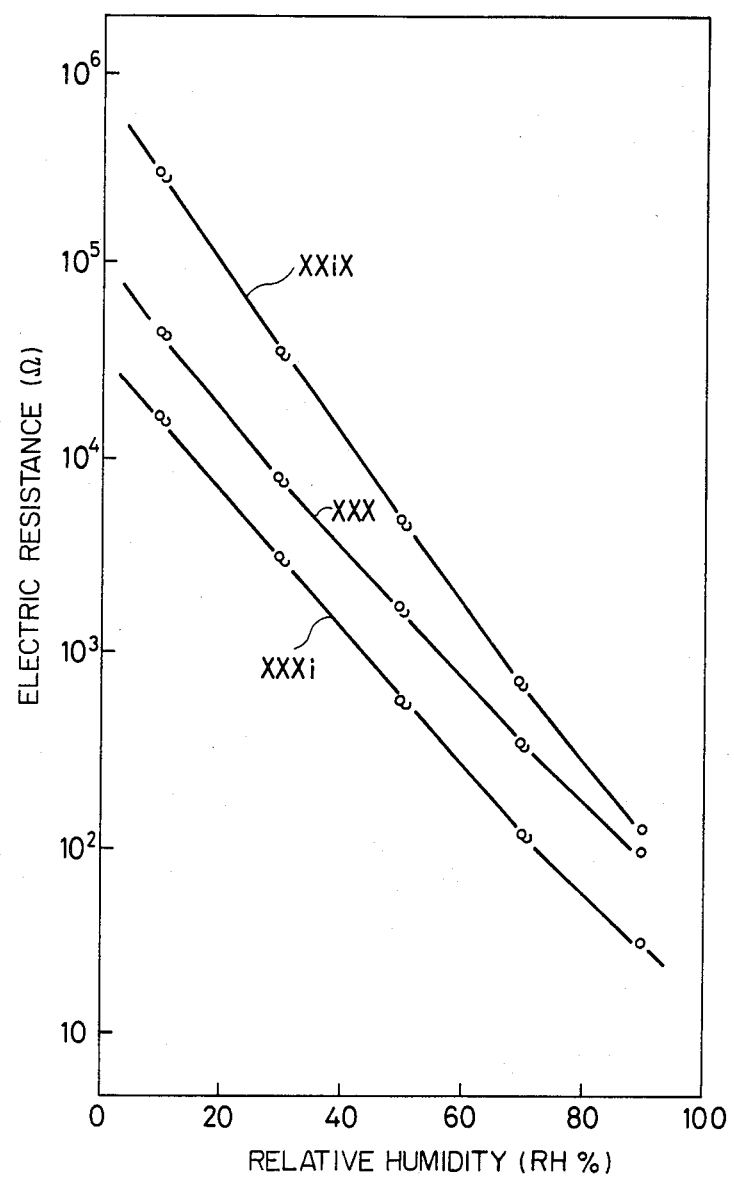

The humidity-sensitive property of the element No. 23 is shown in FIG. 13 by solid line xxix. It may be noted that the time required for the electric resistance to reach equilibrium was not more than 5 minutes at any given humidity. The element No. 23 has low electric resistance, a good linearlity of humidity-sensitive property, and no appreciable hysteresis.

EXAMPLE 21

(METHOD A)

To 300 ml water were added 0.2 mol of acrylonitrile as a hydrophobic monomer, 0.1 mol of vinyltriphenylphosphonium bromide as a cationic monomer and emulsifier, and 0.001 mol of azobisisobutylamidine hydrochloride as a polymerization initiator, and emulsion copolymerization was carried out at 60° C. for 10 hours in nitrogen atmosphere while stirring at a high speed. The resultant latex particles each had a core of polyacrylonitrile and a surface layer containing triphenylphosphonium groups, which are cationic.

This latex was purified by dialysis, then coated on substrate I, and dried by airing. Thus, a humidity sensitive element No. 24 was obtained, of which the coating 8A weighed about 5 mg.

The humidity-sensitive property of the element No. 24 is shown in FIG. 13 by solid line xxx.

EXAMPLE 22

(METHOD B)

To 300 ml water were added 0.2 mol of methyl acrylate as a hydrophobic monomer, 0.01 mol of ethylene glycol dimethacrylate as a cross-linking agent, 0.02 mol of hydroxyethyl methacrylate as a graft site-giving monomer, and 0.02 mol of azobisisobutylamidine hydrochloride as a polymerization initiator, and emulsion polymerization was carried out at 60° C. for 10 hours in nitrogen atmosphere while stirring at a high speed. The resultant latex contained dispersed particles of cross-linked hydrophobic copolymer of methyl acrylate with hydroxyethyl methacrylate. To this latex were added 0.01 mol of cerium (IV) ammonium nitrate as a graft polymerization initiator and 0.1 mol of trimethylvinylammonium bromide as a cationic monomer, and graft polymerization was carried out at 50° C. for 6 hours in nitrogen atmosphere while stirring at a high speed. The resultant latex contained dispersed polymer particles of B-type each comprising hydrophobic polymer having grafting polymer of trimethylvinylammonium bromide.

This latex was purified by dialysis in the same manner as Example 1, then coated on substrate I, and dried by airing. Thus, a humidity-sensitive element No. 25 was obtained, of which the coating 8A weighed about 5 mg.

The humidity-sensitive property of the element is shown in FIG. 13 by solid line xxxi. This element has lower electric resistance than that of the element No. 23 or No. 24.

We claim:

1. A humidity-sensitive element comprising an insulating substrate, a pair of electrodes formed thereon apart from each other by a definite distance, and a coating of humidity-sensitive organic material formed to cover said electrodes, said coating of humidity-sensitive organic material being a synthetic polymer having both a hydrophobic moiety and another moiety selected from the group consisting of an ionic moiety and a hydrophilic moiety, to give the material a property to change its electric resistance depending upon the moisture content in the atmosphere, characterized in that said coating is formed by applying a latex comprising the synthetic polymer to said electrodes, the particles forming said latex having the hydrophobic moiety forming a core of each latex particle and the another moiety forming a surface layer on the core of each latex particle, the material being an aggregate of said particles, with the particles adhering to each other to form a continuous film for the coating.

2. The humidity-sensitive element of claim 1, wherein said another moiety is the hydrophilic moiety.

3. The humidity-sensitive element of claim 1, wherein the synthetic polymer is one prepared by emulsion-copolymerizing at least one nonionic monomer with at least one ionic copolymerizable monomer.

4. The humidity-sensitive element of claim 3, where the nonionic monomer is at least one vinyl compound and the ionic copolymerizable monomer is selected from the group consisting of a monomer having at least one anionic residue selected from the group consisting of sulfonic acid residue, carboxylic acid residue and phosphonic acid residue; and a monomer having at least one cationic group selected from the group consisting of tertiary amino group, a quaternary ammonium group, pyridinium group and phosphonium group.

5. The humidity-sensitive element of claim 3, wherein the nonionic monomer is at least one $\alpha$-ethylenically unsaturated compound selected from the group consisting of an alkyl acrylate, an alkyl methacrylate, $\beta$-hydroxyethylmethacrylate, styrene, acrylonitrile and 4-vinylpyridine, and the ionic copolymerizable monomer is at least one member selected from the group consisting of an alkali metal salt of styrene sulfonic acid, an alkali metal salt of acrylic acid, methacrylic acid, 2-acrylamide-2-methylpropanesulfonic acid, N,N'-dialkylaminoethyl methacrylate, N,N'-dialkylaminoethyl acrylate, N-alkylvinylpyridinium halide, methacryloyloxyethyltrialkylammonium halide, acryloyloxyethyltrialkylammonium halide, 4-vinyl-N-ethylpyridinium halide and vinyltriphenylphosphonium halide.

6. The humidity-sensitive element of claim 1, wherein the synthetic polymer is one prepared by polymerizing at least one ethylenically unsaturated monomer selected from the group consisting of an alkyl acrylate, an alkyl methacrylate and acrylonitrile with hydroxyethyl methacrylate and subjecting the resulting polymer to cross-linking with a monomer having at least two polymerizable double bonds in the molecule selected from the group consisting of ethylene glycol dimethacrylate and divinylbenzene, with the above steps being carried out in an emulsion.

7. The humidity-sensitive element of claim 1, wherein the synthetic polymer is formed by grafting a compound selected from the group consisting of ionic and hydrophilic group compounds onto the surface of particles of a hydrophobic polymer, to provide said particles with said hydrophobic moiety forming said core and said another moiety forming a surface layer on the core.

8. The humidity-sensitive element of claim 1, wherein the latex particles have an average particle size of at most $100\mu$.

9. The humidity-sensitive element of claim 1, wherein the latex particles of the coating have been subjected to a cross-linking treatment.

10. The humidity-sensitive element of claim 1, characterized in that said coating is a coagulated film which is a cluster of said particles, with the surface layer of each particle forming the film being more ionic or more hydrophilic than the core portion of such particle.

11. The humidity-sensitive element of claim 1, characterized in that said surface layer encloses said core.

12. The humidity-sensitive element of claim 11, characterized in that said surface layer is chemically bound to said core.

13. The humidity-sensitive element of claim 1, characterized in that said surface layer is chemically bound to said core.

14. The humidity-sensitive element of claim 1, characterized in that the particles forming the latex, made of the synthetic polymer, are formed by emulsion polymerization, to thereby provide the latex.

15. A humidity-sensitive material, characterized by comprising a plurality of fine particles, each particle having a hydrophobic core and a surface layer formed from a compound selected from the group consisting of an ionic group compound and hydrophilic group compound enclosing said core, said material being an aggregate of said plurality of fine particles, whereby, because of the low moisture absorption of the cores, expansion or shrinkage of a film formed of said material is prevented.

16. The humidity-sensitive material of claim 15, characterized in that said fine particles are those of latex.

17. The humidity-sensitive material of claim 15, characterized in that said compound is grafted onto the surface of said core.

18. The humidity-sensitive material of claim 15, wherein said fine particles are aggregated and formed into a coagulated film, with the particles adhering to each other to form a continuous, coagulated film.

19. The humidity-sensitive material of claim 18, characterized in that said coagulated film is a cluster of said particles, with the surface layer of each particle in the film being more ionic or more hydrophilic than the core portion of such particle.

20. The humidity-sensitive material of claim 15, characterized in that said surface layer is chemically bound to said core for each particle.

21. The humidity-sensitive material of claim 20, characterized in that said fine particles are particles of polymers.

22. The humidity-sensitive material of claim 15, characterized in that the fine particles are made of polymeric material, and are prepared by emulsion-copolymerizing at least one nonionic monomer with at least one ionic copolymerizable monomer.

23. The humidity-sensitive material of claim 15, characterized in that said fine particles are made of a polymeric material, and are formed by emulsion polymerization.

24. A humidity-sensitive element comprising an insulating substrate, said insulating substrate comprising a silicon semiconductor substrate and an electric insulating layer formed thereon, a pair of electrodes formed thereon apart from each other by a definite distance, and a coating of humidity-sensitive material formed to cover said electrodes, said coating of humidity-sensitive material having a property to change its electric resistance depending upon the moisture content in the atmosphere, characterized in that said coating is formed from fine particles each having a hydrophobic core and a surface layer formed from a compound selected from the group consisting of an ionic group compound and a hydrophilic group compound covering said core.

25. The humidity-sensitive element of claim 24, characterized in that said electrodes are a pair of conductive polysilicon elements formed on said electric insulating layer to oppose each other with a narrow space therebetween.

26. The humidity-sensitive element comprising an insulating substrate, said insulating substrate comprising a first electric insulating layer formed of silicon dioxide on a silicon semiconductor substrate and a second electric insulating layer formed of silicon nitride on the first electric insulating layer, a pair of electrodes formed thereon apart from each other by a definite distance, said pair of electrodes being a pair of conductive polysilicon electrodes formed on the second electric insulating layer to oppose each other with a narrow space therebetween, said conductive polysilicon electrodes being formed by implanting phosphorous ions or boron ions into the polysilicon, and a coating of humidity-sensitive material formed to cover said electrodes, said coating of humidity-sensitive material having a property to change its electric resistance depending upon the moisture content in the atmosphere, characterized in that said coating is formed from fine particles each having a hydrophobic core and a surface layer formed from a compound selected from the group consisting of an ionic group compound and a hydrophilic group compound covering said core.

27. The humidity-sensitive element of claim 26, characterized in that connecting terminals are formed on respective end portions of said conductive polysilicon electrodes by vacuum evaporation of titanium, palladium, and gold in this order from bottom to top.

28. The humidity-sensitive element comprising an insulating substrate, a pair of electrodes formed thereon apart from each other by a definite distance, and a coating of humidity-sensitive material formed to cover said electrodes, said coating of humidity-sensitive material having a property to change its electric resistance depending upon the moisture content in the atmosphere, characterized in that said coating is formed from fine particles each having a core of a hydrophobic material and a surface layer of a material having a moiety selected from the group consisting of an ionic moiety and a hydrophilic moiety covering said core, where, because of the low moisture absorption of the cores, expansion or shrinkage and consequent peeling of the coating off the substrate is prevented.

29. The humidity-sensitive element of claim 28, wherein said fine particles are those of latex.

30. A humidity-sensitive element comprising an insulating substrate including a silicon semiconductor substrate and an electric insulating layer formed thereon, a pair of electrodes formed thereon apart from each other by a definite distance, and a coating of humidity-sensitive organic material formed to cover said electrodes, said coating of humidity-sensitive organic material being a synthetic polymer having both a hydrophobic moiety and another moiety selected from the group consisting of an ionic moiety and a hydrophilic moiety, to give the material a property to change its electric resistance depending upon the moisture content in the atmosphere, said coating being formed by applying a latex comprising the synthetic polymer to said electrodes, the particles forming said latex having the hydrophobic moiety forming a core of each latex particle and the another moiety forming a surface layer on the core of each latex particle.

31. The humidity-sensitive element of claim 30, characterized in that said electrodes are a pair of conductive polysilicon electrodes formed on said electric insulating layer to oppose each other with a narrow space therebetween.

32. A humidity-sensitive element comprising an insulating substrate having a first electric insulating layer formed of silicon dioxide on a silicon semiconductor substrate and a second electric insulating layer, formed of silicon nitride, on the first electric insulating layer; a pair of electrodes formed thereon apart from each other by a definite distance, said pair of electrodes being a pair of conductive polysilicon electrodes formed on the second insulating layer to oppose each other with a narrow space therebetween, said conductive polysilicon electrodes being formed by implanting phosphorus ions or boron ions into the polysilicon; and a coating of humidity-sensitive organic material formed to cover said electrodes, said coating of humidity-sensitive organic material being a synthetic polymer having a hydrophobic moiety and another moiety selected from the group consisting of an ionic moiety and a hydrophilic moiety, to give the material a property to change its electric resistance depending upon the moisture content in the atmosphere, said coating being formed by applying a latex comprising the synthetic polymer to said electrodes, the particles forming said latex having the hydrophobic moiety forming a core of each latex particle and the another moiety forming a surface layer on the core of each latex particle.

33. The humidity-sensitive element of claim 32, characterized in that connecting terminals are formed on respective end portions of said conductive polysilicon electrodes by vacuum evaporation of titanium, palladium, and gold in this order from bottom to top.

* * * * *